United States Patent [19]
Goble et al.

[11] Patent Number: 5,425,490
[45] Date of Patent: Jun. 20, 1995

[54] INSTRUMENT WITH DUAL HOLDING FEATURE

[76] Inventors: E. Marlowe Goble, 850 E. 1200 North; David P. Luman, 1430 E. 1260 North, both of Logan, Utah 84321

[21] Appl. No.: 181,840

[22] Filed: Jan. 18, 1994

[51] Int. Cl.⁶ .......................... A61B 17/00; B25C 5/06
[52] U.S. Cl. ..................................... 227/175; 227/147; 606/104; 606/86
[58] Field of Search .................. 606/86, 96, 104, 138, 606/139, 72, 75, 65; 227/147, 175; 81/44, 459

[56] References Cited

U.S. PATENT DOCUMENTS

| | | |
|---|---|---|
| D. 280,550 | 9/1985 | Pratt et al. |
| 2,895,135 | 7/1959 | Hilti ................................... 227/147 |
| 4,263,903 | 4/1981 | Griggs . |
| 4,438,769 | 3/1984 | Pratt et al. |
| 4,462,395 | 7/1984 | Johnson . |
| 4,592,346 | 6/1986 | Jurgutis . |
| 4,723,540 | 2/1988 | Gilmer, Jr. . |
| 4,793,335 | 12/1988 | Frey et al. . |
| 4,960,420 | 10/1990 | Goble et al. ........................... 606/72 |
| 5,013,316 | 5/1991 | Goble et al. . |
| 5,129,902 | 7/1992 | Goble et al. ........................... 606/65 |
| 5,352,229 | 10/1994 | Goble et al. ........................... 606/72 |

OTHER PUBLICATIONS

Howmedica Brochure, Oct., 1986.
1992 Linvatec Catalog, pp. 77 & 81.

*Primary Examiner*—Tamara L. Graysay
*Attorney, Agent, or Firm*—M. Reid Russell

[57] ABSTRACT

A driver instrument with dual holding features for use with a combination of a medical staple and movable washer with that are used in a surgical procedure for attaching a ligament, or the like, onto a bone surface. The driver includes a straight body that is preferably cylindrical, is formed of a hard metal and includes a hand engaging central portion. A driver top end is flanged outwardly into flat head end that can be struck, as with a hammer to impart a hammer force therethrough, with the driver lower end portion formed with a threaded portion for turning into a threaded hole formed through a web of the medical staple, and with a spring collet formed with, or connected axially to, the driver lower end portion. Installation of the medical staple and washer onto the driver involves passing the spring collect through the staple web hole ahead of the driver threaded portion, and through a smooth walled hole formed through the movable washer, with a spring collet ring end passing through the washer hole and restricting removal therefrom. The driver that mounts the medical staple and movable washer, is held by a surgeon to position the staple legs onto a bone surface, straddling a ligament, and then is used to seat the staple into which bone by applying a hammer force to the driver head end. Whereafter, the driver threaded portion is turned out of the staple web threaded hole, pulling also the driver spring collet section out of the washer hole.

9 Claims, 4 Drawing Sheets

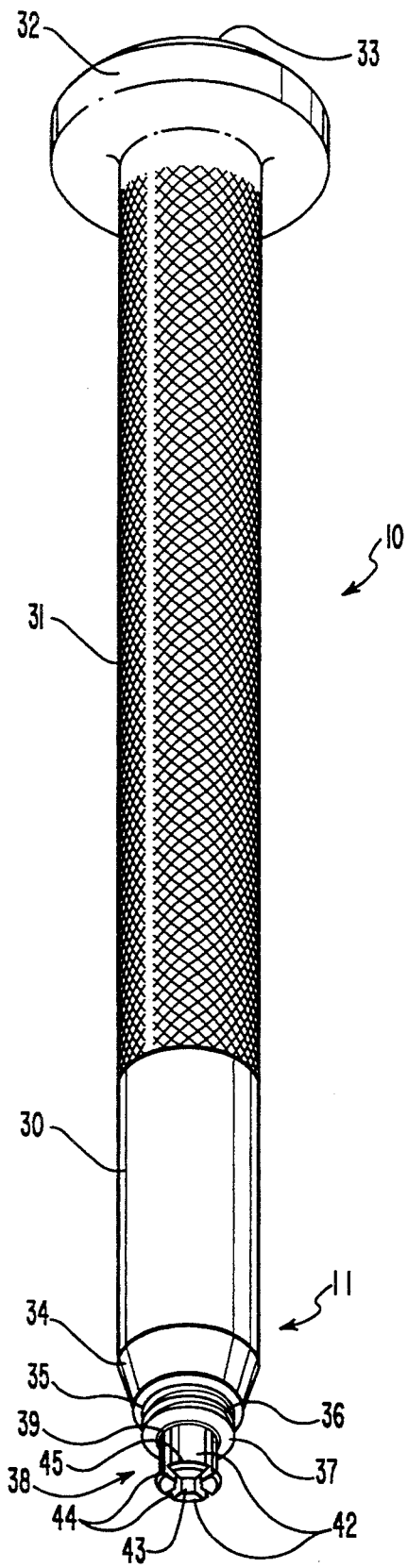
FIG. 1
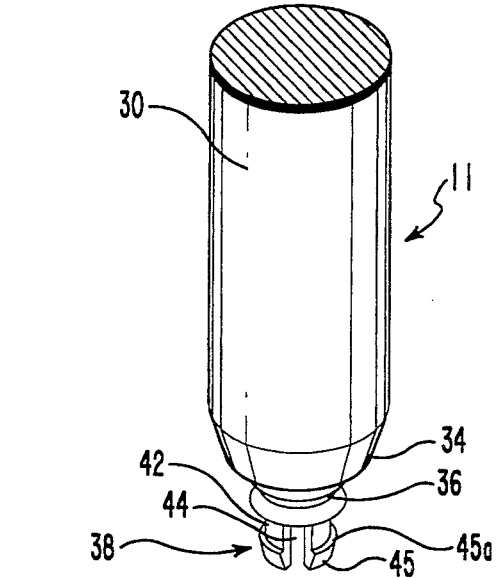
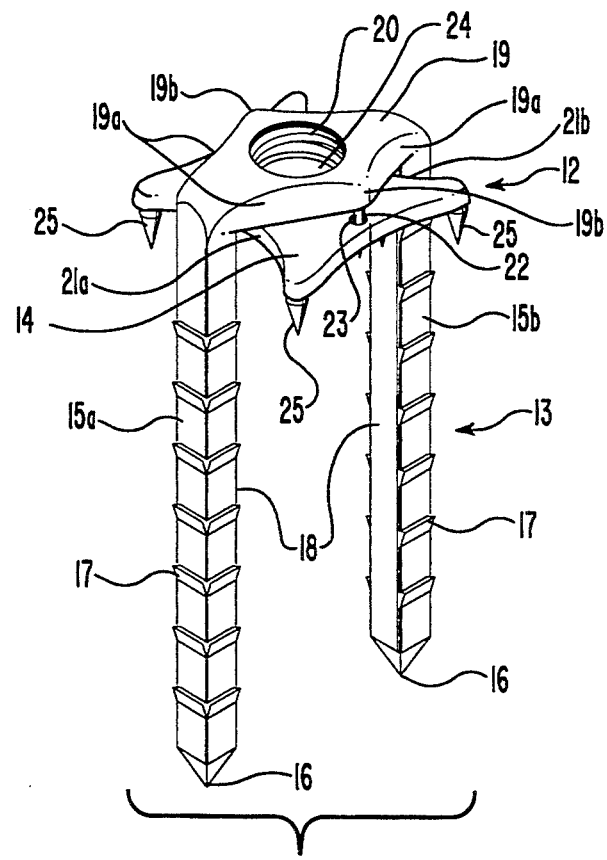
FIG. 2

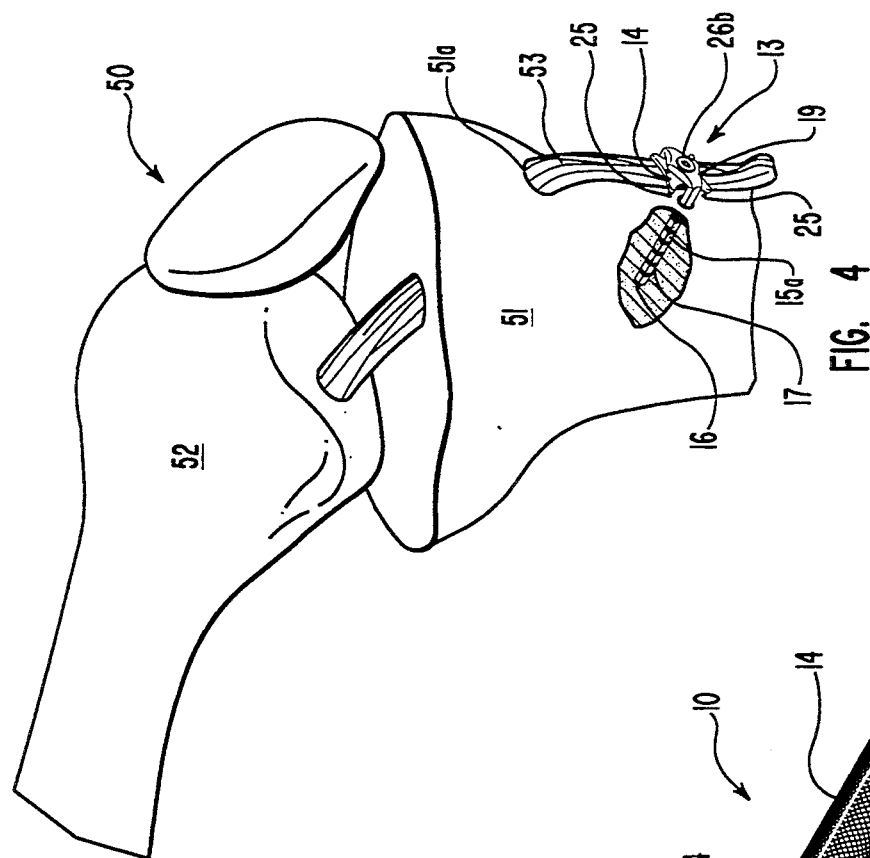
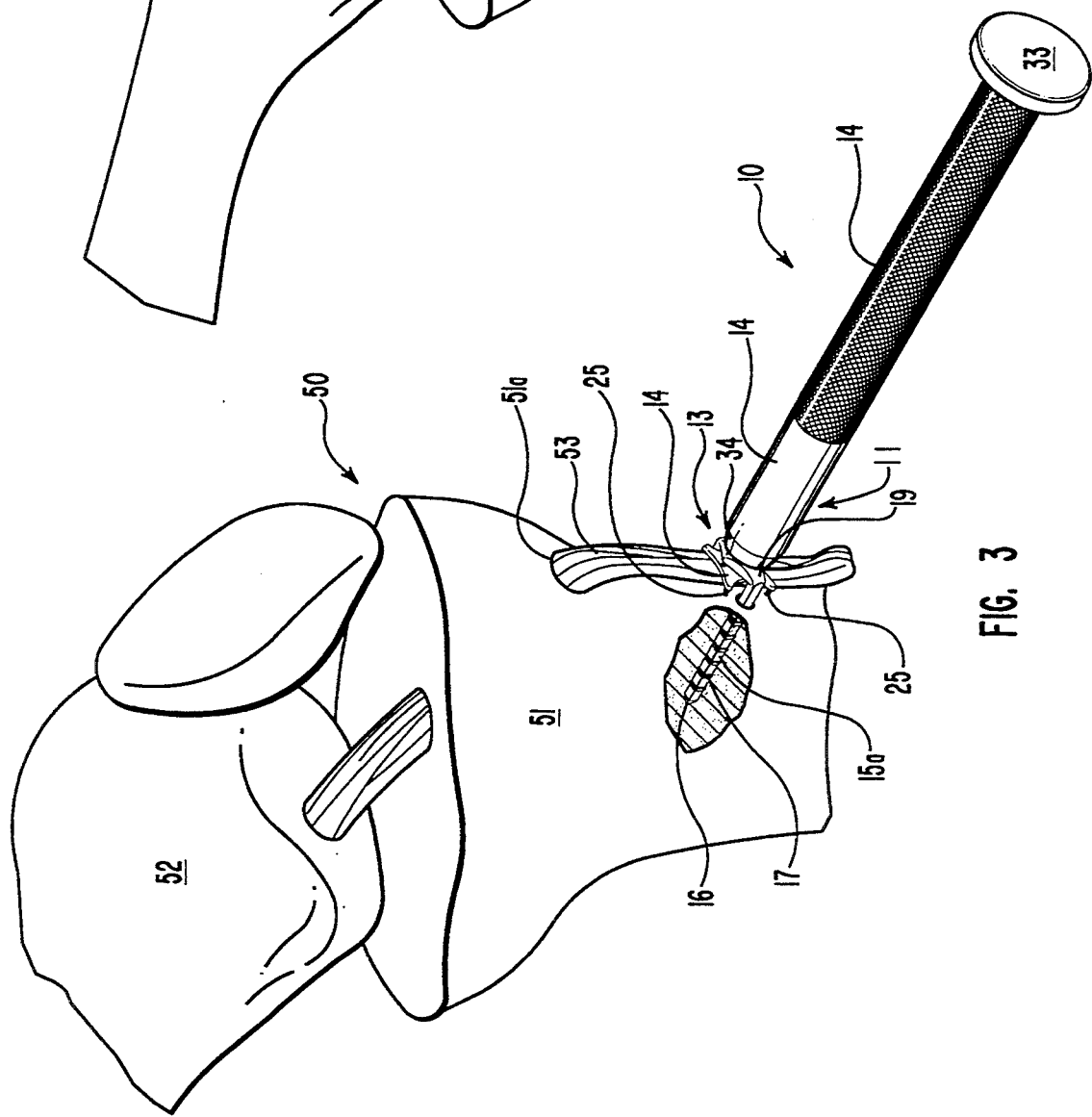

INSTRUMENT WITH DUAL HOLDING FEATURE

BACKGROUND OF THE INVENTION

1. Field of the Invention

This invention relates generally to medical devices for human implantation during orthopedic surgical procedures and more particularly to medical staples and drivers for holding a medical staple during installation.

2. Prior Art

Medical staples are generally for use as attachment devices to maintain a ligament, or the like, onto a bone surface. To this end, the medical staple generally includes two or more legs that are usually straight and parallel, each having a point formed on a leg lower end with the other leg ends maintained to a web member that spans, at approximately a right angle between which legs, forming a U-shape. The staple legs are pointed to facilitate their being driven into a bone by application of a force to the staple web. Such force application is usually directed into the web by a driver that has one end fitted across the staple web with a force applied to the other driver end as with a hammer, or the like. Accordingly, a number of configurations of drivers have been developed for applying a force into a staple web, to urge the staple legs into a bone, with a ligament, or the like, maintained between which staple legs that is thereby clamped by the staple web against the bone surface.

An example of a driver that is positioned on a clamp type device for applying a driving force therethrough to urge spikes and pins of the clamp into a bone is shown in an earlier patent of one of the present inventors, U.S. Pat. No. 4,960,420. Additionally, a number of driver tools that involve opposing jaws have been developed for use with medical staples, where the jaws can either be closed against the staple web opposing sides, or are arranged to receive the staple web slid therebetween. Examples of such drivers are shown in U.S. Pat. No. 4,438,769; and in a 1992 Catalog of Linvatec, as part of a "Staple Fixation System". Examples of driver devices that provide for receiving a staple web between opposing jaws and that include arrangement for applying a clamping force to the opposite web sides, are shown in U.S. Pat. No. 4,263,903; U.S. Pat. No. D. 280,550; and U.S. Pat. No. 4,592,346. Also, for mounting an anchor type device to a driver end, a patent to one of the present inventors, U.S. Pat. No. 5,013,316, includes a threaded driver end for turning onto threaded post that extends axially from the top of the anchor head.

Similar to the driver of U.S. Pat. No. 5,013,316, the invention is a straight cylindrical driver that includes a threaded section on the driver end that is for turning into a threaded hole that has been formed through a web of a medical staple that the invention is preferably utilized with. Additionally, the driver of the invention provides a spring collet as the drive end adjacent to the driver threaded portion, for fitting into and maintaining a washer of the staple. The washer is fitted between to slide along the staple legs, and is to provide for clamping a ligament onto a bone surface wherein the staple is driven. Accordingly, the driver of the invention includes a combination of a spring collet end and threaded portion that are for mounting a staple and washer thereto. In which configuration, the driver is held by a surgeon during staple placement and is for use in driving the staple pointed ends into a bone. Which driver is distinct from the above cited patents and other devices within the knowledge of the inventors.

SUMMARY OF THE INVENTION

It is a principal object of the present invention in a medical instrument with dual holding feature to provide a driver that is preferably for use for mounting a medical staple into a bone, which staple includes a pair of straight staple legs that are each pointed on aligned ends with a web extending between the staple legs opposite ends that has a threaded hole formed therethrough, with a movable washer for arrangement between, to slide along, the staple legs.

Another object of the present invention is to provide a driver type medical instrument that is for mounting a staple and washer combination on an end thereof for guiding pointed ends of the legs of the medical staple to a location on a bone surface and for applying a hammer force therethrough to drive the staple legs pointed ends into the bone.

Another object of the present invention is to provide a driver type medical instrument that has a straight cylindrical body that includes, adjacent to one end, a threaded section that is for turning into a threaded staple web hole and an adjacent spring collet as the driver forward end that is to fit through and seat in straight hole formed through the staple washer.

Still another object of the present invention is to provide a driver type medical instrument that has a solid metal cylinder body to be conveniently gripped by a surgeon and includes a broad head on one end that can be struck by a hammer, or the like, so as to transmit a force therethrough to drive a staple mounted to the other driver end into a bone, the staple web to engage a top surface of a staple washer a drive outstanding pins or spikes extending from the washer undersurface into a ligament, clamping it onto the bone surface.

Still another object of the present invention is to provide a driver type medical instrument that is simple to construct and use for use with a medical staple that includes a movable washer, the driver for mounting the staple and washer to one driver end to both guide staple placement and for transmitting a hammer force into the staple to drive it into a bone surface, the staple web clamping the movable washer against a ligament that has been fitted between the staple legs, securing the ligament onto the bone surface.

The instrument with dual holding feature of the invention is in a driver that is preferably for use with a medical staple identified as "An Arbor Press Staple and Washer" and is the subject of U.S. Pat. No. 5,352,229 of the inventors. The arbor press staple and washer is a medical staple that has straight, equal length, parallel legs that are each pointed on one end and connect at their opposite ends to a web that extends across the legs. The web sides, to form a flat section that is at right angles to the staple legs, slant oppositely outwardly from the staple legs junctions to form oppositely directed center apexes. A flat diamond shaped section is thereby provided wherethrough a threaded center hole is formed. A flat washer is provided that includes concave shaped opposite edges that are spaced apart appropriately to fit between the staple legs, the washer to travel up and down therealong. The washer travel may be guided by guide pins that extend at right angles from the staple web undersurface that fit through aligned holes formed through the washer. The washer includes a smooth walled center hole that, with the washer fitted between the staple legs, aligns with the staple threaded center hole. Further, the washer preferably includes a number of spaced pins or spikes that extend, at right angles, from that washer undersurface for engaging and penetrating a ligament fitted between the staple legs, and to clamp the ligament onto a bone surface when the staple is driven into the bone.

The instrument with dual holding feature of the invention is a driver that is preferably formed as a cylinder and includes a hand gripping central area. A broad flat head is formed across the cylinder upper end that a surgeon can strike, as with a hammer, to apply a force therethrough. The end of the driver opposite to its head end is formed to include a threaded section that is adjacent to a lesser diameter spring collet end. The driver threaded section is of a diameter to easily turn into an arbor press staple web threaded hole, the spring collet travelling therethrough and into a washer smooth walled center hole. The driver spring collet includes a ring end that has a diameter to just fit through the washer smooth hole. The spring collet is slotted at spaced intervals longitudinally to form longitudinal sections that individually flex.

The preferred medical staple and washer is for mounting onto the driver of the invention by fitting the driver spring collet end through the staple web threaded hole and turning the driver threaded section therein. So arranged, the spring collet ring end is to fit through the washer smooth hole. During spring collet ring end travel through the washer hole the spring collet longitudinal sections flex slightly inwardly from the ring end and then flex outwardly to their original attitude when the ring end emerges from the opposite washer side to where the ring end diameter is slightly larger than the washer smooth hole diameter. The spring collet ring end is thereby restricted from return passage back through the washer hole.

With the driver threaded section turned through the staple threaded hole and the driver spring collet ring end fitted through the washer smooth center hole the medical staple and washer are maintained onto the driver end. The driver can thereafter be used to position the staple pointed ends at a location on a bone surface, straddling a ligament, or the like, and can receive a hammer force applied against its head end, to drive the staple pointed ends into the bone to where washer pins or spikes engage the ligament and the washer can be extended away from the staple web after the driver is removed, further clamping the ligament onto the bone surface.

These and other object and features of the present invention will become more fully apparent from the following description taken in conjunction with the accompanying drawings.

DESCRIPTION OF THE DRAWINGS

FIG. 1 is a profile perspective view taken from the bottom end of an instrument with dual holding feature of the invention:

FIG. 2 is a profile perspective view of an arbor press medical staple and washer aligned for receiving a coupling end of the instrument of FIG. 1;

FIG. 3 is a side elevation perspective view of a patient's knee who is undergoing a surgical procedure for the replacement of their anterior cruciate ligament, and showing the instrument of FIG. 1 mounting the arbor press medical staple and washer of FIG. 2 on the end thereof, and showing the instrument of FIG. 1 maintained such that the staple legs are positioned to straddle a ligament end section, with the staple having been driven into the patient's tibia, clamping ligament end against the bone surface;

FIG. 4 is a side elevation perspective view of the patient's knee of FIG. 3 showing the instrument of FIG. 1 removed from the arbor press medical staple and washer and replaced with a threaded pin that has been turned into a threaded hole in the staple web and into engagement with the washer, urging the washer against the ligament;

DETAILED DESCRIPTION

Figure 5:
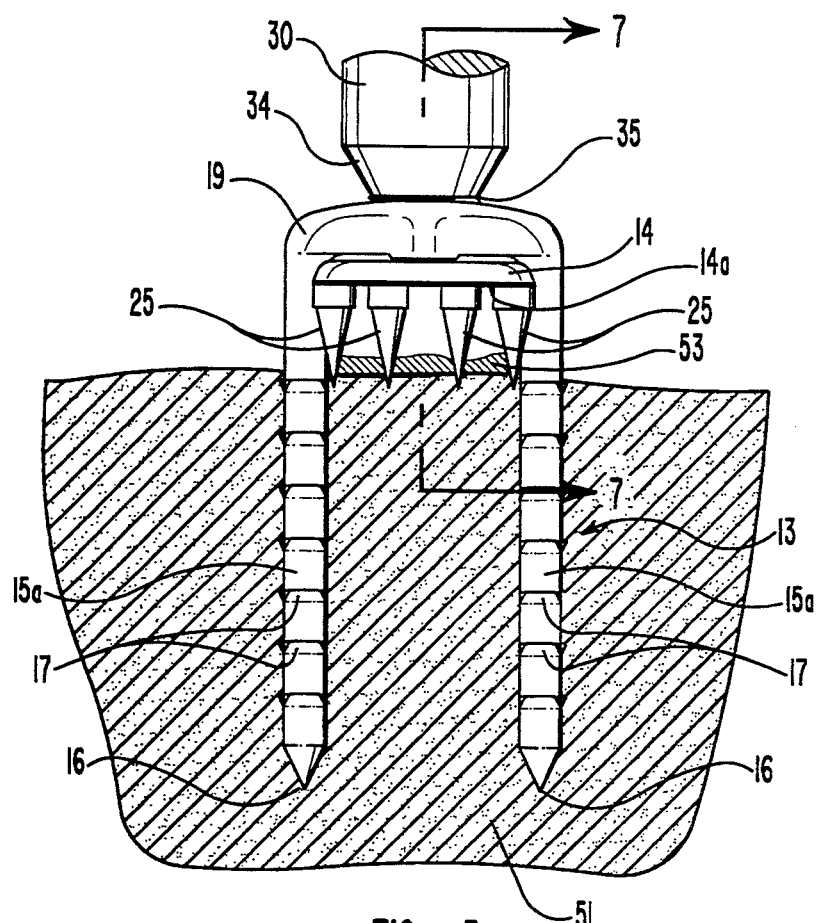
FIG. 5 is an enlarged side elevation view of a coupling end section of the instrument of FIG. 1 that is shown connected to the arbor press medical staple web and washer, and showing the staple legs straddling a section of a ligament, with the staple as having been driven into a bone surface.

A driver type instrument with dual holding feature 10 of the invention is shown in FIG. 1, and is hereinafter referred to as driver 10. In FIG. 2 a lower end 11 portion of driver 10 is shown aligned with a threaded hole 20 of an arbor press staple and washer 12 that the driver 10 of the invention is preferably for use with. The arbor press staple and washer 12 is the subject of U.S. Pat. No. 5,352,229 of the inventors.

The components of the arbor press staple and washer 12 preferably consist of a separate medical staple 13, hereinafter referred to as staple, and a washer 14 that is configured to fit between staple legs 15a and 15b, to travel up or down therealong. As shown, the staple legs 15a and 15b are straight and each has pointed end 16 and includes a plurality of outwardly sloping spaced ridges 17 formed therealong. Each ridge 17 is to extend from around each of the staple legs, leaving smooth staple leg surfaces 18 facing one another. The smooth staple leg surfaces 18 are for accommodating the washer 14 sliding therealong, as set out hereinbelow.

Shown best in FIG. 2, the upper or top ends of the staple legs 15a and 15b connect, at essentially right angles, to ends of a flat web 19, the staple legs and web forming a U shape. The staple web 19, includes a threaded hole 20 formed through a center area thereof, between oppositely outwardly sloping web sides 19a that meet in apexes 19b wherebetween the threaded hole 20 is formed. The washer 14 is shown as a flat section having opposite concave sides 21a and 21b that are for fitting between the staple legs 15a and 15b, engaging the staple legs smooth surfaces 18, to slide therealong. So arranged, the washer 14 is free to move up and down along staple legs 15a and 15b, and is contained therebetween by the ends of the washer concave sides 21a and 21b. In which travel, the washer 14 is preferably guided along guide rods 22 that extend, at right essentially angles, from a staple web undersurface, and are fitted into holes 23 that are formed through the washer. Shown in FIG. 1, and best in FIG. 7, the washer 14 includes a smooth center hole 24 formed therethrough that is for mounting onto a spring collet end of driver 10, as set out in detail hereinbelow.

The washer 14, as shown and described later herein with respect to a discussion of FIGS. 3 through 6, is for engaging so as to clamp a section of a ligament 53 onto a bone surface. Accordingly, as shown best in FIGS. 2 and 5 through 7, washer 14 includes a plurality of spaced pins or spikes 25 that are secured to extend at right angles downwardly from a washer undersurface 14a. In practice, the staple 13, with staple legs 15a and 15b straddling ligament 53, is driven into a bone with the washer pins or spikes 25 to engage the ligament as the washer 14 is urged thereagainst. With the driver 10 removed, the washer then receives a threaded pin 26 turned through the staple web 19, shown in FIGS. 4 and 6, that engages the washer top surface and urges the washer against the ligament 53, the pins or spikes 25 further clamping the ligament against the bone.

Figure 7:
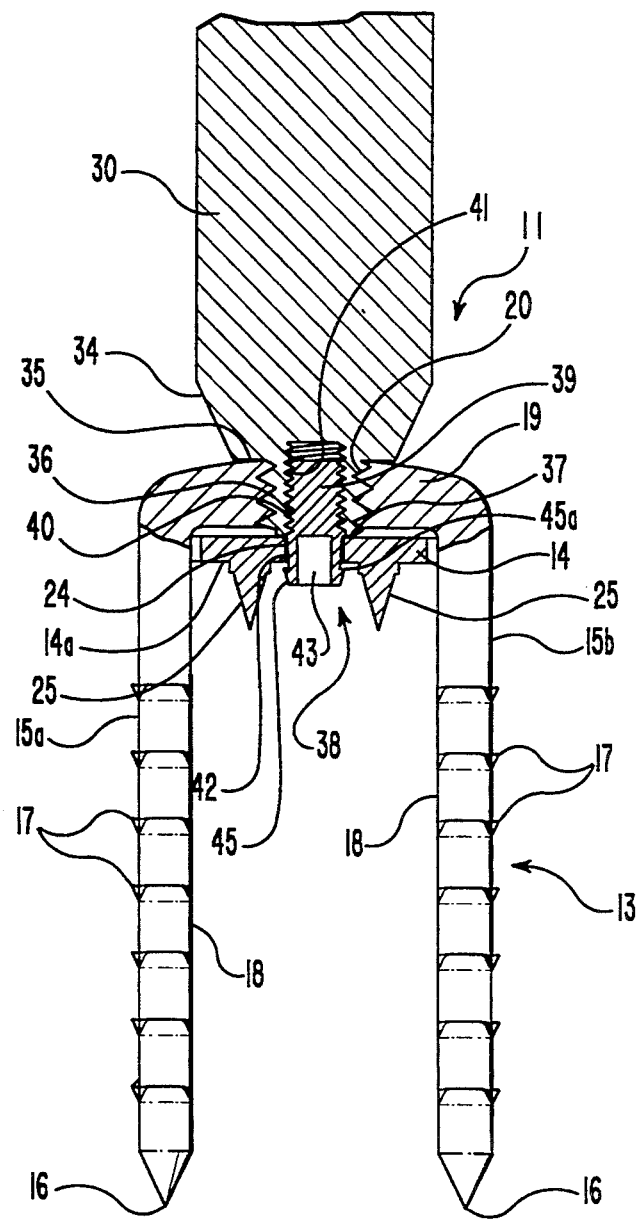
FIG. 7 is an enlarged sectional view taken within the line 7—7 of FIG. 5, showing a removable spring collet segment of the instrument of the invention.

The lower end 11 of the driver 10 of FIGS. 1 and 3 is shown aligned for mounting the staple 13 and washer 14 of FIG. 2, and is shown in FIGS. 5 and 7, with the staple and washer mounted thereon. Driver 10, as shown best in FIG. 1, preferably includes a long cylindrical body 30 that, as shown in FIGS. 2, 5 and 7, can be solid rod stock, and is preferably knurled or scored at 31, as by milling, over a mid-section and upper portion thereof. Which knurling or scoring provides a surface for convenient gripping by a surgeon during a surgical procedure. The driver 10 is flanged outwardly above the scored or knurled portion to form a flat head end 32, having a flat top face 33 that can be struck, as with a hammer, to transmit a hammer force through the driver. Such hammer force is transmitted through the driver body 30 into the lower end 11 portion thereof. The body 30 is preferably smooth below the scored section 31 and is sloped inwardly at 34 into the lower end portion 11.

Shown best in FIGS. 1, 2 and 7, the lower end of slope 34 of body 30 is cut inwardly into a right angle face 35 that terminates in a driver threaded section 36. The driver threaded section 36 has a same diameter and threads as the threads of threaded hole 20 that is formed in the staple web 19, the threaded section 36 to turn therein. So arranged, the driver threaded section 36 is turned into the web threaded hole 20 to mount the staple 13 thereon. Below the driver threaded section 36 the driver is formed into an end face 37 that terminates in a spring collet 38 that extends axially from the center of the end face 37. The spring collet 38 can be machined from the body 30, but is preferably separately formed to have a body that is removable, as illustrated in FIG. 7.

FIG. 7 shows a cavity drilled axially into the center of the driver lower end portion 11 end face 37 that has been tapped to form threads 40. The threads 40 are to receive a threaded end 41 of spring collet body 39 turned therein. The spring collet body lower end section is formed as a smooth walled cylinder 42 that is open longitudinally at 43 and has longitudinal slots 44 cut radially at equal spaced intervals therearound, forming spring collet sections. The spring collet 38 preferably also includes a ring 45 formed around its end that is also cut by slots 44, forming ring sections on the ends of the spring collet sections. The spring collet 38 is formed of a material that is sufficiently resilient to allow the spring collet sections to flex inwardly when a compressive force is applied around the ring 45. Such compression force is provided when the ring 45 is urged into a hole than has a slightly smaller diameter than the ring 45 outside diameter. The spring collet sections will thereby flex inwardly and will return to their original attitude when the compressive force is removed therefrom. Accordingly, when the spring collet ring 45 is fitted into the smooth walled washer 14 hole 24, that has a smaller diameter than the ring 45 outside diameter, the spring collet sections will be flexed inwardly as the spring collet 38 is urged through hole 24. But will return to their original altitude, urging a ring 45 rent flat wall surface 45a, shown best in FIG. 2, over the edge at the washer lower face of hole 24, as shown in FIG. 7.

In practice, as shown best in FIG. 7, the driver threaded section 36 is turned into the staple web 19 threaded hole 20 to mount the staple thereto. In which mounting, the washer 14 that is held against the undersurface of the staple web 19, receives the driver spring collet 38 ring 45 that passes through the washer 14 smooth hole 24 as the driver threaded section 36 is turned into the staple web threaded hole 20. In which passage, the spring collet sections are flexed inwardly during ring passage, and then flex outwardly as the ring passes beyond the edge of washer hole 24. The ring flat wall surface 45a is thereby slid over the washer hole edge, mounting the washer onto the spring collet 38.

As set out above, the staple 13 and washer 14 are mounted onto the driver 10 that a surgeon manipulates to position the staple leg 15a and 15b pointed ends 16 at a location on a bone surface. The selected bone surface, shown in FIG. 3, is a proximal tibia 51 of a patient's knee 50 that includes a distal femur 52. So arranged, the staple 13 legs straddle a ligament 53. The ligament 53 is for installation as a replacement for the patient's anterior cruciate ligament in a knee surgical procedure that involves mounting a ligament 53 femoral end endosteally in a closed tunnel as has been formed into the patient's femur. In which procedure, the ligament tibial end extends beyond a proximal tibia tunnel opening 51a, and a surgeon applies a tensile force to the tibial ligament end as the staple 13 is positioned thereover. So arranged, a hammer force can then be applied to the driver 10 head end 32 face 33 that is transmitted into the staple legs 15a and 15b pointed ends 16 so as to urge the staple legs into the tibia 51, as shown in FIGS. 3 and 5. The washer undersurface pins or spikes 25 are thereby urged towards and into the ligament 53 surface. Thereafter, the driver 10 is removed by turning the driver threaded section 36 out of the staple web 14 threaded hole 20. Which threaded section removal also pulls the driver spring collet 38 end out of the washer 14 smooth hole 24, leaving the staple and washer mounted onto bone 51.

Figure 6:
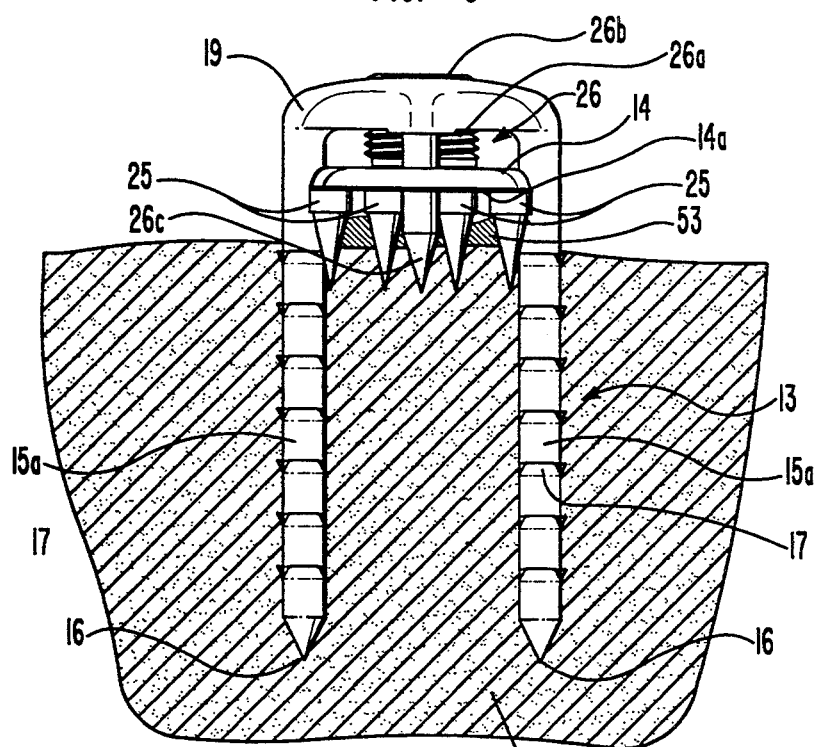
FIG. 6 is a view like FIG. 5 with the instrument of the invention removed and showing a threaded pin turned through the staple web to engage the washer to urge it against the ligament, clamping the ligament onto the bone surface.

With the staple and washer mounted to bone 51, as shown in FIG. 5, a threaded section 26a of threaded pin 26, shown in FIGS. 4 and 6, can then be turned into staple web threaded hole 20 by fitting and turning an appropriate tool, such as an ALLEN wrench, not shown, into a recess that has been formed in a head end 26b of threaded pin 26. Turning of threaded pin 26 in the web threaded hole 20 urges a pointed end shaft 26c of which threaded pin 26, as shown in FIG. 6, through the washer 13 smooth center hole and through ligament 53. In which turning of the threaded pin 26 into threaded hole 20, a shoulder at the junction of the threaded pin threaded section 26a and shaft 26c engages the edge of the top surface of the washer 14 hole 24 to urge it away from the staple web 19. The washer 14 is thereby moved into clamping engagement into the ligament 53, as shown in FIGS. 4 and 6, with the threaded pin 26 shaft 26c pointed end traveling through the ligament 53 and into bone 51, securely clamping the ligament onto the bone surface.

While a preferred embodiment of the invention in an instrument with dual holding feature for use with a staple and washer has been shown and described herein, it should be understood that the present disclosure is made by way of example only and that variations to the described device and its uses are possible within the scope of this disclosure without departing from the subject matter coming within the scope of the following claims, and a reasonable equivalency thereof, which claims we regard as our invention.

We claim:

1. An instrument for mounting a medical staple and accompanying movable washer comprising, an instrument body formed as a straight section from a rigid material having an upper proximal end and a lower distal end, said upper proximal end having a top end that is flared outwardly relative to said instrument body, said lower distal end having a threaded section and a spring collet section, said threaded section having a first outer diameter, with said spring collet section having a proximal end and a distal end, and said spring collet section comprises a hollow cylinder having a second outer diameter that is less than said threaded section first outer diameter and at least a pair of spaced longitudinal slots are formed therein from the distal end, with said distal end of said spring collet section including a ring that has a third outer diameter that is greater than said hollow cylinder second outer diameter and is less than said threaded section first outer diameter.

2. An instrument with dual holding feature as recited in claim 1, wherein the instrument body is scored around a mid-section thereof as a gripping surface.

3. An instrument with dual holding feature as recited in claim 1, wherein the instrument body is formed from solid metal round stock.

4. An instrument with dual holding feature as recited in claim 1, wherein the instrument body is sloped inwardly to form an inverted cone section that terminates in a step at a proximal end of said threaded section.

5. An instrument with dual holding feature as recited in claim 1, wherein the spring collect includes a threaded proximal end and the instrument body adjacent to a distal end of the threaded section wherein is formed a tapped hole that is extends axially into the center of said instrument body.

6. An instrument with dual holding feature as recited in claim 1, wherein the spring collet section ring end has a rounded forward facing surface and is flattened into a flat wall section around a rear facing surface.

7. An instrument for mounting a medical staple and accompanying movable washer comprising, an instrument body formed as a straight section from a rigid material having an upper proximal end and a lower distal end, said upper proximal end having a flat top surface, and said lower distal end having a threaded section and a spring collet section, said threaded section having a first outer diameter, with said spring collet section having a proximal end and a distal end, and said spring collet section comprises a hollow cylinder having a second outer diameter that is less than said threaded section first outer diameter and at least a pari of spaced longitudinal slots are formed therein from the distal end, with said distal end of said spring collet section including a ring that has a third outer diameter that is greater than said hollow cylinder outer diameter and is less than said threaded section first outer diameter.

8. An instrument with a dual holding feature as recited in claim 1, wherein the spring collect section is arranged to be separable form the instrument body and includes a connection means at its proximal end for connection to the instrument body adjacent to the threaded section.

9. An instrument with a dual holding feature as recited in claim 1, wherein the spring collet ring distal end has a tapered forward facing surface and is flattened into a flat wall section around a rear facing surface.

* * * * *